(12) United States Patent
Stein et al.

(10) Patent No.: US 6,468,522 B1
(45) Date of Patent: Oct. 22, 2002

(54) CONTROLLED RELEASE OF THIOAMIDE MOIETY-CONTAINING THERAPEUTIC AGENTS

(75) Inventors: Stanley Stein, East Brunswick, NJ (US); Guobao Zhang, Piscataway, NJ (US); Bo Qiu, New Brunswick, NJ (US)

(73) Assignees: University of Medicine and Dentistry of New Jersey, New Brunswick, NJ (US); Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/621,109

(22) Filed: Jul. 21, 2000

Related U.S. Application Data

(60) Provisional application No. 60/145,177, filed on Jul. 22, 1999.

(51) Int. Cl.[7] .......................... A61K 31/74; A61K 39/44; A61K 9/14
(52) U.S. Cl. ................. 424/78.28; 424/78.27; 424/486; 424/181; 424/DIG. 16
(58) Field of Search ........................... 424/78.28, 78.27, 424/486, 181.1, DIG. 16

(56) References Cited

PUBLICATIONS

Nathan, A., Zalipsky, S., Ertel, S.I., Agathos, S. N., Yarmush, M.L. and Kohn, J. (1993) Copolymers of lysine and poly(ethylene glycol): A new family of functionalized drug carriers. Bioconj. Chem. 4, 54–62.

Woghiren, C., Sharma, B. and Stein, S. (1993) Protected thiol–polyethylene glycol: A new activated polymer for reversible protein modification. Bioconj. Chem. 4, 314–318.

Zabicky, J. The Chemistry of Amides, P449, Interscience Publishers (1970).

Huang, S., Pooyan S., Wang, J., Choudhury, I., Leibowitz, M.J., and Stein, S. (1998) A polyethylene glycol copolymer for carrying and releasing multiple copies of cystein–containing peptides, Bioconj. Chem. 9, 612–617.

Borkow, G., Barnard, J., Nguyen, T. M., Belmonte, A., Wainberg, M. A., Parniak, M. A. Chemical barriers to human immunodeficiency virus type 1 (HIV–1) infection: Retrovirucidal activity of UC781, a thiocarboxanilide nonnucleoside inhibitor of HIV–1 reverse transcriptase. J. Virol. 71, 3023–3030.

(List continued on next page.)

*Primary Examiner*—Thurman K. Page
*Assistant Examiner*—Blessing Fubara
(74) *Attorney, Agent, or Firm*—Klauber & Jackson

(57) ABSTRACT

This invention pertains to disulfide-linked conjugates of therapeutic agents containing at least one thioamide group with polymer comprising at least one thiol group, so as to provide a controlled release pharmaceutical composition for administration to animals for the prophylaxis or treatment of various conditions or diseases. The therapeutic agent conjugate may comprise an inactive or weakly active prodrug form which may be converted into the original therapeutic compound by the natural action of reducing agents in vivo. The composition may comprise a mixture of polymers each with a different thioamide-containing agent attached, or a polymer conjugated with a mixture of thioamide-containing agents. Modified properties of the therapeutic compound potentially provided by the polymer itself, as well as by other compounds also appended to the polymer, include but are not limited to greater water solubility, longer in-vivo half-life (due to larger size of the conjugate), slower release from a sustained-release depot (due to larger size of the conjugate), better oral bioavailability and tissue-specific targeting.

59 Claims, 9 Drawing Sheets

OTHER PUBLICATIONS

Kirpotin, D et al (1996) Liposomes with detachable polymer coating: destabilization and fusion of dioleoyphosphatidylethanolamine vescles triggered by cleavage of surface–granted poly(ethylene glycol). FEBS Letters, 388(2/03), 115–118 (Abstract as provided by ISA).

Vincentelli, Jean et al. (1996) Poly(ethylene glycol) derivatized prodrugs through mixed disulfide bond formation: Preliminary report on captopril, International Journal of Pharmaceutics, 134(1–2), 147–155.

Vincentelli et al. "Poly(ethylene glycol) derivatized prodrugs through mixed disulfide bond formation:preliminary report on captopril," International Journal of Pharmaceutics, 134(1–2), 147–155, 1996.*

* cited by examiner

TLC (ethyl acetate/hexane: 20/80) of UC781 dimer formation reaction

Lane 1. UC781  Lane 2. UC781 dimer formation reaction mixture 1    2

TLC (Ethyl acetate/Hexane :20/80 ) of PEG-S-S-UC781 cleavage reaction

Lane 1: UC781, Lane 2: PEG-S-S-UC781, Lane 3: PEG-S-S-UC781 with DTT, Lane 4: DTT alone 1 2 3 4

FIG. 6A
FIG. 6B
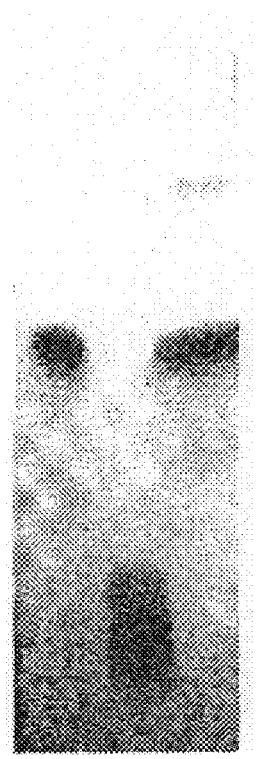
1 2 3
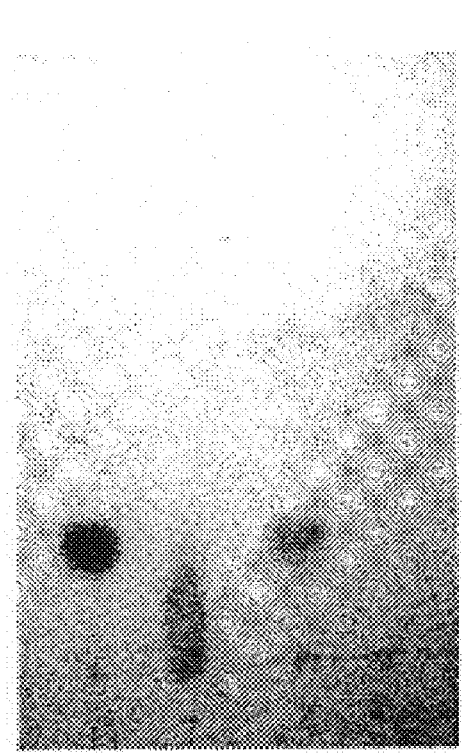
4 5 6 7

CONTROLLED RELEASE OF THIOAMIDE MOIETY-CONTAINING THERAPEUTIC AGENTS

CROSS-REFERENCE TO RELATED APPLICATION

This application claims priority to provisional application Ser. No. 60/145,177, filed Jul. 22, 1999, and is incorporated herein by reference in its entirety.

FIELD OF THE INVENTION

This invention pertains to disulfide-linked conjugates of therapeutic agents containing at least one thioamide group with thiol-containing polymers, so as to provide a controlled release pharmaceutical composition for administration to animals for the prophylaxis or treatment of various conditions or diseases.

BACKGROUND OF THE INVENTION

Derivatives of polymers such as polyethylene glycol (PEG) containing thiol (—SH) groups may be used as a controlled release carrier for therapeutic agents with thiol groups, by administering the polymer to which the therapeutic agent is linked by a disulfide bridge. Reduction of the disulfide group by endogenous reducing agents results in the release of the therapeutic agent (Huang et al.[10]; Woghiren et al.[19]). Furthermore, the therapeutic agent linked to the polymer may be in an inactive, or prodrug form, which when released becomes active. The inclusion of various targeting agents which also have been conjugated to the same polymer to target the therapeutic agent to particular sites within the body or to enhance cellular uptake have been described.

Appended PEG chains may provide the favorable pharmacologic properties of protection of the underlying protein from immune surveillance and proteolytic enzymes, in addition to a lower rate of clearance from the bloodstream (Davis et al., 1981). Furthermore, based on the properties provided by the PEG portion of the conjugate (Davis et al., 1981), conjugates of therapeutic agents as prodrugs with polymers provides certain advantages such as reduction in possible toxicity, since biological activity of a large bolus of that drug would not appear immediately upon administration to the patient. Thus, the biological activity might be present at a relatively constant, therapeutic level in the bloodstream over an extended time period due to two opposing actions, the conversion of inactive prodrug to active drug and the clearance of active drug from the body.

While therapeutic agents which have a thiol group, or may be derivatized to have one without loss of activity, are suitable for the above process, numerous other compounds without such groups cannot be bound to thiol-containing polymers following standard procedures to produce a controlled release composition. This is particularly true for compounds with a thioamide group. It is toward the development of a controlled release delivery system for therapeutic agents with thioamide groups that the present application is directed.

The citation of any reference herein should not be construed as an admission that such reference is available as "Prior Art" to the instant application.

SUMMARY OF THE INVENTION

In its broadest aspect, the present invention is directed to a pharmaceutical composition which is a disulfide-linked conjugate between at least one therapeutic agent comprising prior to conjugation a thioamide moiety, and at least one polymer comprising prior to conjugation at least one thiol group. The polymeric portion of the polymer which comprises prior to conjugation at least one thiol group may be a homopolymer or a copolymer, and may be by way of non-limiting example, polyethylene glycol, carboxymethylcellulose, dextran, polyvinyl alcohol, N-(2-hydroxypropyl)methacrylamide, polyvinyl pyrrolidone, poly-1,3-dioxolane, poly-1,3,6-trioxane, polypropylene oxide, copolymers of ethylene/maleic anhydride copolymer, polylactide/polyglycolide copolymers, polyaminoacids, copolymer of polyethylene glycol and an amino acid, or polypropylene oxide/ethylene oxide copolymers. The polymer may also be a branched polymer or a dendrimer, i.e., a multi-branched polymer.

In a preferred embodiment, the polymer is a polyethylene glycol polymer (PEG), for example, of a molecular weight of from about 300 to about 30,000 Da, and preferably, from about 600 to about 5,000 Da. The PEG has functional groups or may be derivatized to bear functional groups to which a compound providing a free thiol group may be attached. The polymer comprising at least one thiol group may have from one to about ten thiol groups per polymer; preferably from one to about three thiol groups per polymer. The thiol group on the polymer may be sterically hindered.

The polymer comprising at least one thiol group may be prepared from, for example, $\alpha,\omega$-diamino-polyethylene glycol and thiomalic acid; $\alpha,\omega$-dihydroxy-polyethylene glycol and thiomalic acid; $\alpha,\omega$-dicarboxy-polyethylene glycol and cysteamine; $\alpha,\omega$-dicarboxy-poly(ethylene glycol) and 1-amino-2-methyl-2-propanethiol; or $\alpha,\omega$-dicarboxy-PEG subunits and lysine, wherein carboxy groups on the lysines are derivatized to form thiol groups. The selection of the thiol compound providing the disulfide link to the thioamide-containing compounds and the covalent link to the polymer may be selected from a number of compounds containing a thiol group and a reactive group which may be attached to a polymer.

The therapeutic agent comprising prior to conjugation a thioamide moiety may be an agent that contains such a thioamide group in its active form, or a therapeutic agent which is modified to contain a thioamide group. For example, therapeutic agents with thioamide groups include UC781; R82150; HBY097; troviridine; S2720; UC38 and 2',3'-dideoxy-3'-fluoro-4-thiothymidine. However, the invention is not so limiting. Furthermore, other compounds with thioamide-like groups of similar reactivity to thioamide-containing compounds as described herein are likewise suitable as compositions as described herein. Such compounds include but are not limited to thioureas and thiourethans.

In a further aspect of the invention, the polymer may additionally have a functional group, which may be derivatized with a compound such as but not limited to a cell uptake enhancer or a tissue targeting agent.

The composition of the present invention may include a second therapeutic agent, or a second and a third therapeutic agent. This may be achieved by preparing polymers conjugated to each therapeutic agent separately, and then mixing these polymers to provide a composition with more than one therapeutic agent. In another embodiment, a single polymer to which at least two thiol groups is attached may be derivatized with a mixture of therapeutic agents. The relative amounts of the different agents conjugated to the polymer may be selected to correspond with the therapeutic effectiveness of each compound. The therapeutic agents conjugated to the polymer of the invention are released in vivo under reducing conditions. The in-vivo half life of the therapeutic agent in the composition may be increased compared with that of the therapeutic agent alone in vivo. Furthermore, the therapeutic agent may be therapeutically inactive or weakly active in the composition. The water solubility of the therapeutic agent may be increased in said composition compared to its inherent water solubility.

In another broad aspect, the invention is directed to a pharmaceutical composition which is a disulfide-linked conjugate between at least one therapeutic agent comprising prior to conjugation a thioamide moiety, a bifunctional compound comprising prior to conjugation at least one thiol group, and at least one polymer attached to one or more of the bifunctional compounds. The polymer may be a homopolymer or a copolymer, and may be by way of non-limiting example, poly(ethylene glycol), carboxymethylcellulose, dextran, polyvinyl alcohol, N-(2-hydroxypropyl)methacrylamide, polyvinyl pyrrolidone, poly-1,3-dioxolane, poly-1,3,6-trioxane, polypropylene oxide, copolymers of ethylene/maleic anhydride copolymer, polylactide/polyglycolide copolymers, polyaminoacids, copolymer of polyethylene glycol and an amino acid, or polypropylene oxide/ethylene oxide copolymers. The polymer may also be a branched polymer or a dendrimer, i.e., a multi-branched polymer. For linkage to the bifunctional compound, the polymer may have one or more similar or different functional groups such as an amino or carboxy group, which may be cross-linked to the functional group on the bifunctional compound with a cross-linking agent, or the polymer may be an activated polymer, such as but not limited to polyethylene glycol bis(imidazoyl carbonyl), which is capable of reacting with an amino group. The bifunctional compound comprising prior to conjugation at least one thiol group may for example comprise a thiol group and an amino group, such as but not limited to cysteamine or 1-amino-2-methyl-2-propanethiol.

In another broad aspect of the present invention, methods for preparing a composition comprising a disulfide-linked conjugate of at least one therapeutic agent comprising prior to conjugation a thioamide moiety with at least one polymer comprising prior to conjugation at least one thiol group are described. The conjugate may be prepared by following the steps of: (A) providing at least one therapeutic agent comprising a thioamide moiety or modified to have a thioamide moiety; (B) providing at least one polymer comprising at least one thiol group; (C) reacting the at least one therapeutic agent comprising a thioamide moiety under oxidizing conditions to form a disulfide cross-linked dimer of the therapeutic agent comprising a thioamide moiety; (D) reacting the disulfide-linked dimer with the polymer comprising at least one thiol group, under conditions in which a disulfide exchange reaction occurs to form a disulfide-linked conjugate between the therapeutic agent comprising a thioamide moiety, and the at least one polymer comprising at least one thiol group; and (E) isolating the disulfide-linked conjugate.

The thiol-containing polymer may have a thiol-containing moiety thereon, which may be prepared by any of a number of methods. By way of non-limiting example, a compound with a thiol group and another functional group, for example, an amino group, may be covalently coupled to a polymer with carboxylic acid moieties, for example, 1-amino-2-methyl-2-propanethiol or cysteamine may be conjugated to a PEG polymer with carboxylic acid moieties, using a carbodiimide reagent. By way of another example, thiol-containing compounds containing a carboxylic acid moiety such as thiomalic acid may be conjugated to a PEG bearing amino moieties using a carbodiimide. In the previous examples, the thiol group of 1-amino-2-methyl-2-propanethiol is sterically hindered, while that of cysteamine is less so.

The polymer comprising at least one thiol group may be prepared from, for example, α,ω-diamino-poly(ethylene glycol) and thiomalic acid; α,ω-dihydroxy-poly(ethylene glycol) and thiomalic acid; α,ω-dicarboxy-poly(ethylene glycol) and cysteamine; α,ω-dicarboxy-poly(ethylene glycol) and 1-amino-2-methyl-2-propanethiol; or α,ω-dicarboxy-PEG subunits and lysine, wherein carboxy groups on the lysine are derivatized to form thiol groups. The selection of the thiol compound providing the disulfide link to the thioamide-containing compounds and the covalent link to the polymer may be selected from a number of compounds containing a thiol group and a reactive group which may be attached to a polymer.

In a further aspect of the invention, methods for preparing a composition comprising a disulfide-linked conjugate between at least one therapeutic agent comprising prior to conjugation a thioamide moiety, a bifunctional compound comprising prior to conjugation at least one thiol group, and at least one polymer attached to one or more bifunctional compounds are described. In one embodiment, a disulfide exchange-produced heterodimer is prepared between the thioamide-containing compound and a bifunctional compound comprising at least one thiol group and an amino group, thus forming a disulfide-linked conjugate comprising the therapeutic agent and the functional (amino) group. Subsequently, the functional group of the heterodimer is covalently linked to the polymer, for example, using a cross-linking reagent to cross-link the functional group of the bifunctional compound and a functional group on the polymer, or by use of an activated polymer capable of reacting directly with the functional group on the bifunctional compound. In yet a further embodiment, the bifunctional group comprising a thiol group is first conjugated to the polymer, for example by any of the foregoing methods, leaving at least one free thiol group, and subsequently, a homodimer of the oxidized therapeutic agent is reacted under disulfide exchange conditions with the polymer to produce the desired conjugate. In this fashion, additional control over the selection of sterically hindered thiol groups is provided to tailor the release characteristics of the therapeutic agent to the particular condition to be treated or prevented, and the target organ, tissue or cells.

The polymer portion of the polymer comprising at least one thiol group and the bifunctional compound are as described hereinabove.

The therapeutic agents in the present invention have a thioamide group, whether present in or introduced synthetically into the agent. For example, the agent may be UC781; R82150; HBY097; troviridine; S2720; thiouridine; UC38 and 2',3'-dideoxy-3'-fluoro-4-thiothymidine. Many other therapeutic agents, for various uses, are embraced herein. Furthermore, a therapeutic agent may be prepared or chemically modified to provide a therapeutically active analog having a thioamide group.

The oxidizing conditions to form the dimer of the thioamide-containing therapeutic agent comprises reaction in the presence of an oxidizing agent which may include, but is not limited to, molecular oxygen, hydrogen peroxide, and molecular iodine. The subsequent disulfide exchange reaction may be carried out under conditions which promote the reaction, for example, in a degassed nonaqueous solvent, such as a 1:1 mixture of dimethylformamide and dichloromethane. The invention is not so limiting to these conditions and any suitable conditions may be employed to achieve the preparation of the desired conjugate.

Furthermore, any therapeutic agent having a thioamide-like group that may be oxidized to form a dimer and then attachable via a disulfide exchange reaction to a thiol-containing polymer via a disulfide bond is suitable for use herein. Such moieties such as but not limited to thioureas and thiourethans are included herein.

The polymer comprising at least one thiol group may additionally have a functional group, such as an amino or carboxyl group, and by way of non-limiting examples, the additional functional group is optionally derivatized with a cell uptake enhancer or a tissue targeting agent. The polymer may also be a branched polymer or a dendrimer, i.e., a multi-branched polymer.

A pharmaceutical composition of the present invention prepared as described above may have a second therapeutic agent or a second and third therapeutic agent. The preparation step may include a mixture of disulfide-linked dimers of more than one agent, which during the disulfide exchange reaction become conjugated to the polymer. The relative efficiency of disulfide exchange and/or the relative concentration for each dimer may be used to provide conditions such that the resulting polymer has the therapeutic agents present at the desired ratio. In another embodiment, polymers conjugated separately to particular therapeutic agents following the process described above are mixed at the desired ratio before administration to the patient.

The therapeutic agent is of the composition released in vivo under reducing conditions. The in-vivo half life of said therapeutic agent in the composition may be increased compared with that of the therapeutic agent alone in vivo. Furthermore, the therapeutic agent may be therapeutically inactive or weakly active in the composition. The water solubility of the therapeutic agent may be increased in said composition compared to its inherent water solubility. In a further embodiment, the disulfide-linked agent polymer conjugate may be entrapped in a matrix providing a controlled release depot.

In another aspect of the present invention, a method is provided for the controlled release in an animal of at least one therapeutic agent having a thioamide moiety comprising administering to the animal a composition comprising a pharmaceutical composition as described hereinabove. The composition may comprise a second therapeutic agent, or a second and a third therapeutic agent. The therapeutic agent may be released in vivo under reducing conditions.

The in-vivo half life of said therapeutic agent in the animal is increased compared with that of the therapeutic agent alone in said animal. The therapeutic agent may be therapeutically inactive or weakly active in said composition.

In another aspect of the present invention, a method is provided for the controlled release in an animal of a therapeutic agent within a preselected body compartment comprising administering to said animal a composition comprising the pharmaceutical composition as described above, wherein the pharmaceutical composition additionally comprises a targeting agent for targeting said composition to said compartment. Non-limiting examples of targeting agents include an antibody, a cell uptake enhancer, or a tissue targeting agent.

These and other aspects of the present invention will be better appreciated by reference to the following drawing and Detailed Description.

BRIEF DESCRIPTION OF THE DRAWING

FIG. 6 shows the results of TLC of 4-thiouridine reactions.

DETAILED DESCRIPTION OF THE INVENTION

Figure 1:
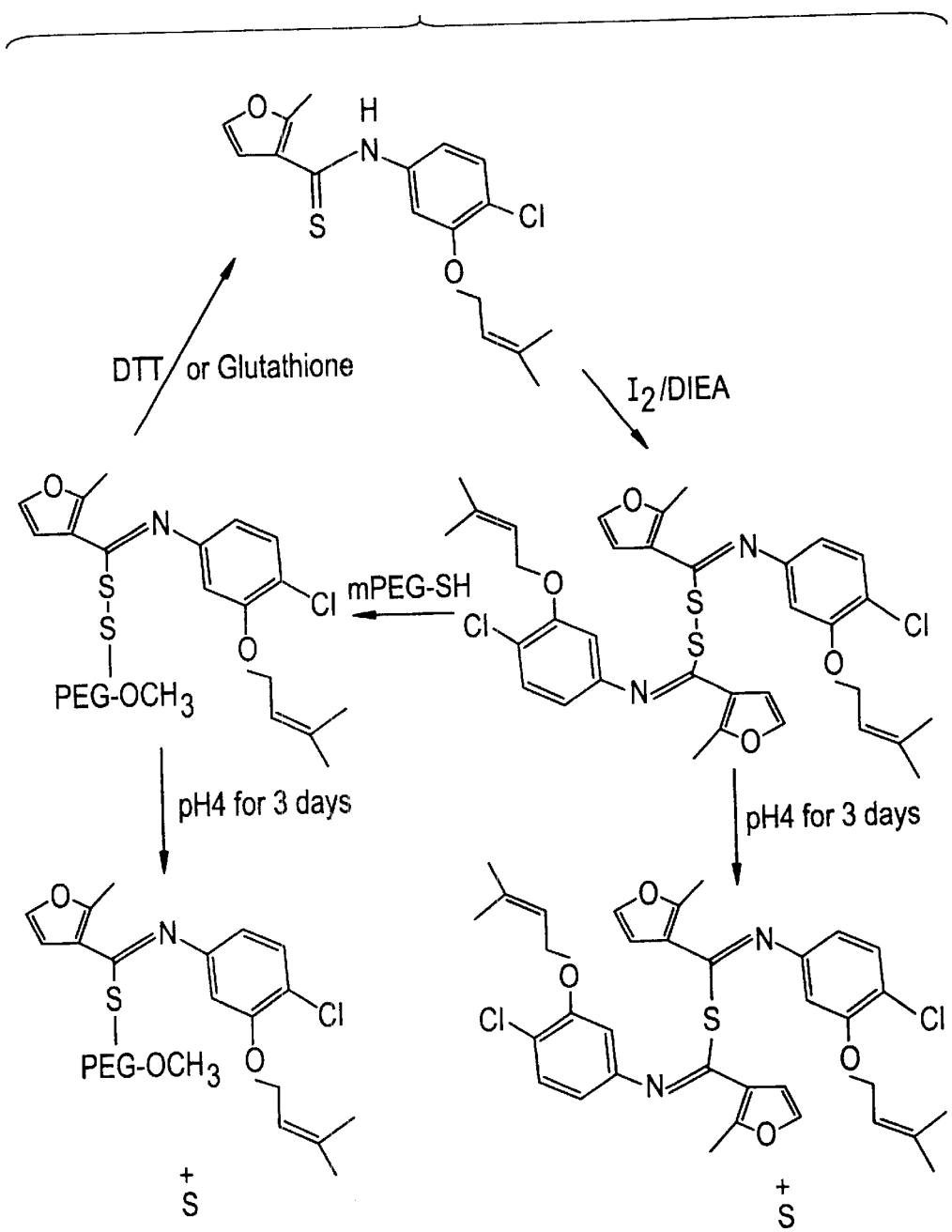
FIG. 1 depicts the reactions for the synthesis of a conjugate between a PEG modified with thiol groups and UC781 (referred to as PEG-S-S-UC781), and for the regeneration of the original active drug, UC781. Side reactions giving sulfur elimination are also shown.

This invention is directed to disulfide-linked conjugates of therapeutic agents comprising at least one thioamide group with a polymer comprising at least one thiol group, so as to provide a controlled release pharmaceutical composition for administration to animals for the prophylaxis or treatment of various conditions or diseases. The therapeutic agent conjugate may comprise an inactive or weakly active prodrug form which may be converted into the original therapeutic compound by the natural action of reducing agents in vivo. The composition may comprise a mixture of polymers each with a different thioamide-containing agent attached, or a polymer conjugated with a mixture of thioamide-containing agents. Modified properties of the therapeutic compound potentially provided by the polymer itself, as well as by other compounds also appended to the polymer, include but are not limited to greater water solubility, longer in-vivo half-life (due to larger size of the conjugate), slower release from a sustained-release depot (due to larger size of the conjugate), better oral bioavailability and tissue-specific targeting.

The compositions of the present invention comprise disulfide-linked conjugates between a polymer comprising prior to conjugation at least one thiol group and therapeutic agents containing a thioamide moiety prior to conjugation, or a polymer attached to a bifunctional compound which is disulfide-linked with a therapeutic agent comprising prior to conjugation a thioamide group. These conjugates have a general structure $R^1-N=C(R^2)-S-S$-polymer or polymer-$F_2-F_1-X-S-S-C(R^2)=N-R^1$. As will be described in more detail below, the thiol group of the polymer of bifunctional compound, respectively, may be derived from a compound covalently attached to the polymer or compound, providing the thiol group and optionally a means for sterically hindering the thiol group to provide particular characteristics of the composition, such as susceptibility to reducing agents and consequent release rate. As used herein, the phrase "therapeutic agent comprising prior to conjugation a thioamide moiety," refers to a conjugate in which a reactant is a compound having a thioamide moiety (—NH—C=S); however, this moiety is present in the form of a —N=C—S— moiety in the conjugate. Moreover, the phrase "polymer comprising prior to conjugation at least one thiol group" may refer both to a polymer derivatized to comprise thiol group(s), or to a conjugate of a polymer comprising a functional group and a bifunctional compound as described herein, in both instances providing a polymer subsequently conjugatable to a thioamide compound by the methods herein to form the final disulfide-linked thioamide compound as described herein.

The present invention extends to therapeutically useful compounds having at least one thioamide group (—NH—C=S). By way of non-limiting example, compounds with thioamide groups include several reverse transcriptase inhibitor (RTI) compounds useful for HIV/AIDS therapy or prophylaxis, as well as those with moieties of similar reactivity, including: UC781; R82150; HBY097; troviridine; S2720; UC38 and 2',3'-dideoxy-3'-fluoro-4-thiothymidine, and are applicable to the preparation of the compositions of the present invention. Furthermore, other compounds with thioamide-like groups of similar reactivity to thioamide-containing compounds as described herein as likewise suitable for the preparation of a composition as described herein. Such compounds include but are not limited to thioureas (e.g., R82150 and trovirdine) and thiourethans (e.g., UC38). The term thioamide used herein embraces thioamides as well as the related structures mentioned above, as well as their relatives. Model therapeutic compounds with a thioamide moiety, such as thiouridine, is also embraced herein.

UC781, chemically known as N-[4-chloro-3-(3-methyl-2-butenyloxy)phenyl]-2-methyl-3-furancarbothioamide, was described by Borkow et al. (18). R82150, chemically known as (+)-S-4,5,6,7-tetrahydro-5-methyl-6-(3-methyl-2-butenyl)-imidazo[4,5,1-jk][1,4]-benzodiazepin-2(1H)-thione, was described by Pauwels et al., 1990. Troviridine, or LY-300046, is N-[2-(2-pyridylethyl)-N'-[2-(5-bromopyridyl)]thiourea. HBY 097, known chemically as (S)-7-methoxy-3,4-dihydro-2-[(methylthio)methyl]-3-thioxo-2(1H)-quinoxalinecarboxylic acid, isopropyl e was described by Kleim et al., 1997. UC-38 is 4-chloro-3-(isopropoxycarbonyl)phenyl-carbamothioic acid, O-isopropyl ester. 3'-F-4-thio-ddT, an abbreviation for 2',3'-dideoxy-3'-fluoro-4-thiothymidine, was described by Matthes et al., 1989.

Examples of suitable subunit polymers comprising at least one thiol group include both homopolymers or copolymers. By way of non-limiting example, suitable polymers, which may have modifications to attach thiol group(s), include poly(ethylene glycol) [also known as polyethylene glycol or PEG, polyethylene oxide or PEO], carboxymethylcellulose, dextran, polyvinyl alcohol, N-(2-hydroxypropyl) methacrylamide, polyvinyl pyrrolidone, poly-1,3-dioxolane, poly-1,3,6-trioxane, polypropylene oxide, copolymers of ethylene/maleic anhydride copolymer, polylactide/polyglycolide copolymers, polyaminoacids, copolymer of polyethylene glycol and an amino acid, or polypropylene oxide/ethylene oxide copolymers. By way of illustration, described in more detail below with regard to the methods for preparing the compositions, such polymers are then derivatized or further polymerized to introduce thiol groups; chemical modification of the polymer may be necessary as a step prior to the further derivatization to incorporate thiol groups. For example, a copolymer of the present invention may be derived from a poly(ethylene glycol) (PEG) derivative, for example, α,ω-dihydroxy-PEG, αω-dicarboxy-PEG or α,ω-diamino-PEG, but other derivatives are embraced herein. The polymer comprising thiol groups may be, for example, α,ω-diamino-poly(ethylene glycol) and thiomalic acid; α,ω-dihydroxy-poly(ethylene glycol) and thiomalic acid; α,ω-dicarboxy-poly(ethylene glycol) and cysteamine; αω-dicarboxy-poly(ethylene glycol) and 1-amino-2-methyl-2-propanethiol; or a copolymer of α,ω-dicarboxy-PEG subunits and lysine wherein the free carboxy groups on said lysine are derivatized to form thiol groups. These polymers are only examples of possible choices, as the skilled artisan will be aware of numerous alternatives. As will be noted below, the selection of the polymer, or combinations thereof, will be guided by the desired properties of the final product, particularly the duration of release of the therapeutic agent and the release kinetics. As will also be noted below, a product of the invention may comprise more than one polymer component in order to provide two or more different release characteristics. Of course, more than one therapeutic agent may be included.

The polymer is preferably PEG. Thiol-PEG (MW=5 kDa) may be purchased from Fluka, but thiol-PEG of different molecular weights or with multiple thiol-attachment sites may be used. A combination of 2 or more drugs may be appended on the multivalent PEG in a preselected ratio. Furthermore, moieties with other functions, such as cell uptake enhancement or tissue-selective targeting, may be appended to the multivalent PEG. Such cell uptake enhancement compounds have been described. Although PEG has been used for the Examples given below, substitution of PEG by another biocompatible thiol-containing polymer is within the scope and spirit of this Invention.

In one particular embodiment, a copolymer of the present invention is derived from a poly(ethylene glycol) (PEG) derivative, for example, α,ω-dihydroxy-PEG, α,ω-dicarboxy-PEG or α,ω-diamino-PEG, but other derivatives are embraced herein. Examples of such polymers with particular molecular weights include α,ω-dihydroxy-PEG$_{3,400}$; α,ω-dihydroxy-PEG$_{1,000}$; α,ω-diamino-PEG$_{3,400}$; and α,ω-diamino-PEG$_{1,000}$. PEG is known to be a particularly nontoxic polymer. One commercially-available polymer with a thiol group useful for the practice of the present invention is O-(2-mercaptoethyl)-O'-methyl polyethylene glycol 5000 (mPEG-SH; 5000 Da).

In the embodiment wherein a bifunctional compound is provided in the conjugate which is disulfide-linked to the thioamide-containing agent as well cross-linked to the polymer, several examples of conjugates between polymers and bifunctional agents comprising at least one thiol group are described above, such as cysteamine, thiomalic acid, etc., conjugated to PEG, for example using a homobifunctional or heterobifunctional cross-linking agent. In an alternate embodiment, an activate polymer capable of directly reacting with the functional group on the bifunctional compound may be employed, such as, in the example of a bifunctional compound comprising a thiol group and an amino group, the activated polymer polyethylene glycol bis(imidazolyl carbonyl), from Sigma Chemical Co., will react with amino groups to form the conjugate.

In an example of the preparation of a therapeutic agent of the invention, a dimer of UC781 may be prepared by oxidation with iodine. Conversion to the dimer by oxidation may be monitoring by thin layer chromatography (TLC), to indicate the nearly complete conversion as compared to the original UC781 monomer. The dimer is subsequently purified. Then, mPEG-SH as described above and the UC781 dimer are reacted to form PEG-S-S-UC781, and the product purified therefrom.

In another strategy, the UC781 homodimer is prepared as described above, but then converted by disulfide exchange into a heterodimer with another bifunctional thiol compound, for example, with 1-amino-2-methyl-2-propanethiol hydrochloride or cysteamine, both of which also contain an amino group. This UC781 heterodimer comprising an amino group is then appended to a polymer, such as α,ω-dicarboxy-PEG by amide bond formation, using the amino group on the heterodimer, by use, for example, of a carbodiimide. As noted above, direct cross-linking of the amino group to the polymer may be achieved with an activated polymer.

The foregoing examples are not meant to be limiting and other reactants and processes are embraced herein for preparing the compounds described herein.

In another example, a copolymer of α,ω-dicarboxy-PEG subunits and lysine may be prepared, and subsequently the free carboxy groups on the lysine are derivatized to form thiol groups. These examples are provided by way of illustration only and such methods for adding a thiol group to a polymer are known to one skilled in the art.

The polymer comprising at least one thiol group may have from one to about ten thiol groups per polymer; from one to about three thiol groups per polymer is preferred. The polymer comprising at least one thiol group may have a molecular weight of from about 300 to about 30,000 k Da, preferably from about 600 to about 5,000 Da.

The thiol group on the thiol-containing polymer may be sterically hindered. For example, when an intermediate bifunctional compound, such as the amino- and thiol-containing compound in the second method above, is used between the thioamide-containing compound and the polymer, a sterically hindered thiol group such as is present in the compound 1-amino-2-methyl-2-propanethiol decreases the releasability of the thioamide-containing compound in the presence of reducing agents such as glutathione. If a compound with a less-sterically-hindered thiol group such as cysteamine is used, the conjugate is more easily reduced by reducing agents. By judicious selection of the intermediate thiol/amine-containing compound and the degree of steric hindrance of the thiol group, a range of release over 2–3 logs may be selected. Thus, the desired release characteristics for a particular compound for a particular target organ or tissue, as well as other kinetic parameters, may be built into the composition of the present invention by following the guidance herein.

The present invention is also directed to methods for the preparation of the compositions described hereinabove. The compositions are prepared from a polymer comprising at least one thiol group, depicted as polymer-SH, and a thioamide-containing compound, depicted with the structural formula $R^1$—NH—$C(R^2)$=S. The methods described herein provide for the preparation of the conjugate, which has the structural formula $R^1$—N=$C(R^2)$—S—S-polymer. The following steps are carried out, in schematic form, and will be described in more detail below:

1. Oxidation:
   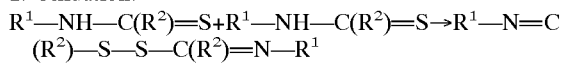

2. Disulfide exchange:
   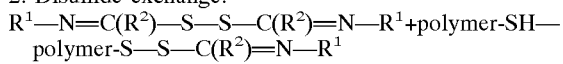

$R^1$—N=$C(R^2)$—S—S—$C(R^2)$=N—$R^1$+polymer-SH—
   polymer-S—S—$C(R^2)$=N—$R^1$ In vivo, under reducing conditions, a reducing agent, such as glutathione, depicted as R—SH, reduces the polymer to release the therapeutic agent: Polymer-S—S—$C(R^2)$=N—$R^1$+R—SH→$R^1$—NH—$C(R^2)$=S+polymer-S—S—R.

The conjugate may derived from the two reactants described above, but as it will be shown below, the two reactants cannot simply be reacted under oxidizing conditions to form the disulfide bond. The preparation of the conjugate is carried out by first oxidizing the thioamide-containing agent to form homodimers, and then performing a disulfide exchange reaction between the dimer and the polymer comprising at least one thiol group, forming the conjugate. The details of this reaction will be elaborated upon below.

As noted above, a direct oxidation of the thioamide compound with the thiol-containing polymer does not achieve the preparation of the conjugate of the present invention. A disulfide exchange reaction is performed between the thiol-containing polymer or thiol-containing compound and dimers prepared by the oxidation of the thioamide-containing agent. Various other methods of preparation are embraced within the present invention to achieve the preparation of the desired product; these will be described further below. In one example, the following steps are carried out with the reactants. First, the therapeutic agent comprising a thioamide moiety is reacted under oxidizing conditions to form disulfide cross-linked dimers of the therapeutic agent. The oxidizing conditions entail the reaction in the presence of an oxidizing agent, for example, by molecular oxygen, hydrogen peroxide, or molecular iodine. Other oxidizing conditions for forming dimers of the thioamide-containing agent are embraced herein; the skilled artisan will be aware of other suitable agents and conditions for preparing the dimer.

After preparation of the dimer, a disulfide exchange reaction is performed in the presence of the polymer comprising at least one thiol group, to form the desired conjugate. The conditions for performing this reaction are also known by the skilled artisan. For example, the reaction between the dimer and the polymer may be performed in a degassed nonaqueous solvent, such as a 1:1 mixture of dimethylformamide and dichloromethane. However, the reaction conditions for the preparation of the product described here is not so limiting and may be practiced by any one of a number of suitable conditions.

It is important that the reaction conditions employed to permit the disulfide exchange reaction to proceed does not result in a rearrangement reaction in which an atom of sulfur is eliminated from the disulfide linkage, thereby forming a thioether-linked dimer (Schaeffer et al., 1967; Zabicky, 1970). Such an undesirable reaction can be caused by the inappropriate application of heat, or the carrying out of the reaction at a low pH, for example, around pH 4. The elimination of sulfur will produce a product in which the thioamide-containing compound is conjugated to the polymer through a single sulfur atom, and the conjugate is not reducible to yield the free therapeutic agent and polymer.

By way of example of the aforementioned procedure, dimers of UC781 are prepared by oxidation in the presence of iodine. Next, the UC781 dimers are mixed with a thiol-containing polymer, O-(2-mercaptoethyl)-O'-methyl polyethylene glycol 5000 under conditions favoring disulfide exchange. The product is subsequently purified.

The releasability of the therapeutic agent from the polymer by reaction with reducing agents is easily demonstrated, as shown below in Example 1.

In another embodiment for the preparation of the compositions herein, the thioamide-containing therapeutic agent may be oxidized as described above to form disulfide-linked homodimers of the agent. The homodimers are then, by disulfide exchange, reacted with a thiol-containing compound with a functional group (depicted as $F_1$-X—SH) to produce heterodimers, and subsequently, the heterodimers are linked to a polymer through a functional group on the polymer. The polymer with a functional group is depicted as $F_2$-polymer. The reactions are depicted as follows, and described in more detail below.

1. Oxidation:

2. Disulfide exchange with thiol-containing compound.:

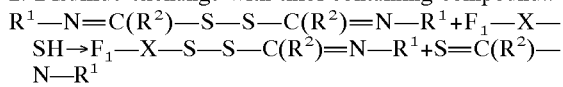

3. Conjugation of functional groups:

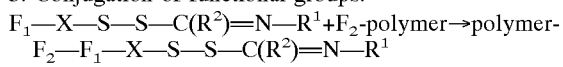

The preparation of the homodimers under oxidizing conditions are as described above. Subsequently, the homodimers may be reacted in the presence of a thiol-containing bifunctional compound such as, by way of non-limiting example, cysteamine or 1-amino-2-methyl-2-propanethiol, under disulfide exchange conditions, forming heterodimers of the therapeutic agent and the bifunctional thiol-containing compound. After purification of the desired heterodimers, they may be conjugated to a polymer by taking advantage of functional groups on both the polymer and the bifunctional thiol-containing compound. For example, the aforementioned thiol-containing compounds have amino groups, which may be coupled to carboxy groups on the polymer, for example, dicarboxy-PEG, using a carbodiimide reaction. Other cross-linking agents, including homobifunctional and heterobifunctional agents, may be used to achieve the desired product. The final product must be sensitive to reducing conditions in order that the thioamide-containing therapeutic agent is released from the disulfide link under the appropriate reducing conditions. The skilled artisan will be aware of the criteria needed for the selection of the appropriate reaction scheme and conditions, to increase yield and ensure stability of the reactants and product. The process may be performed with a reduced number of steps depending on the reactivity of the reactants and the tolerable yield and ease in purification of the desired intermediates or products from byproducts.

For example, UC781 homodimers are prepared as described in Example 1 below. Subsequently, 1-amino-2-methyl-2-propanethiol hydrochloride is added under conditions to favor disulfide exchange, and the heterodimer product is purified using a silica gel column. The heterodimers are then reacted with polyethylene glycol bis(imidazolyl carbonyl) to directly form the final conjugate. The product is then purified.

As mentioned above, the composition of the present invention may comprise a plurality of different therapeutic agents attached to a single type of thiol-containing polymer with at least two thiol groups, or may be a mixture of different polymers of at least one thiol group each containing a different agent. These variations allow controlled delivery of multiple agents at a predetermined ratio.

In a further embodiment of the present invention, the pharmaceutical compositions comprising at least one thioamide agent may also be derivatized with a functional group, such as an amino or carboxyl group. These functional groups may optionally serve as sites for attachment of other compounds or agents, such as a targeting agent for targeting said composition to said compartment. Such compounds as antibodies, cell uptake enhancers, and tissue targeting agents may be employed.

As will be seen in the examples below, administration of the polymer comprising UC781 of the invention to mice or rabbits results in release of UC781 in vivo, demonstrating the in-vivo reductive cleavage of the polymer as expected. Moreover, further experiments on blood samples from animals administered the polymer comprising UC781 demonstrate reverse transcriptase activity, confirming biological activity of the compound released in vivo.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Synthesis and Analysis of a Reversible Conjugate, PEG-S—S-UC781.

Figure 2:
FIG. 2 shows thin layer chromatography demonstrating conversion of UC781 into disulfide-linked homodimer. Detection was by UV shadowing.

1. Preparation of UC781 dimer. UC781 (MW 335 Da, 165 mg, 0.5 mmol) was dissolved in 10 ml of ethyl ether and cooled to 0° C., and 87 μL (0.5 mmol) of diisopropylethyl amine (DIEA) was added to this solution. Then 63.5 mg iodine (0.25 mmol) was dissolved in 10 ml of ethyl ether and cooled to 0° C. The iodine solution was added to the UC781 solution dropwise while stirring in an ice bath. The reaction was allowed to go for 4 hours. On thin layer chromatography (TLC) (ethyl acetate/hexane: 20/80), the reaction mixture gave a new spot (Rf=0.6) with nearly complete conversion (FIG. 2), compared to the original UC781 monomer (Rf= 0.4). The salt, diisopropylethyl ammonium iodide, precipitated and was filtered through paper. The product was taken to dryness and used without further purification.

II. Preparation of PEG-S—S-UC781. O-(2-mercaptoethyl)-O'-methyl polyethylene glycol 5000 (mPEG-SH; 5000 Da) was from Fluka. mPEG-SH (50 mg, 0.01 mmol) and 20 mg of UC781 dimer were dissolved in a degassed, mixed solvent of 1 ml dimethylformamide and 1 ml of dichloromethane (DCM). The reaction mixture was kept under argon overnight. TLC (ethyl acetate/hexane: 20/80) showed a spot remaining at the origin, indicating the formation of the PEG-S—S-UC781 product, since mPEG-SH cannot otherwise be seen by UV shadowing and since any PEG compound would be expected to remain at the origin. The DCM was then evaporated and the product was recovered by ether precipitation of the reaction mixture in 10 ml of cold ether. The product was washed four times with 5 ml of cold ether, and TLC showed only one spot remaining at the origin (FIG. 3), indicating complete removal of unreacted UC781 monomer and dimer. Spectroscopic analysis of the conjugate showed a broad band of absorption in the WV, similar to that of the original UC781.

Figure 3:
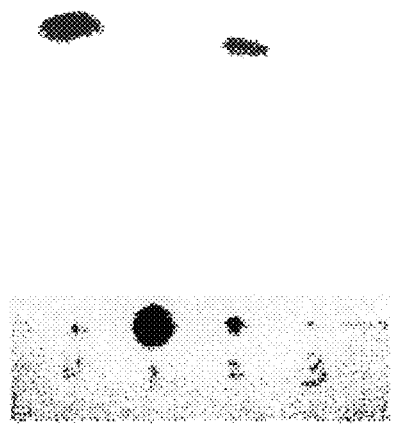
FIG. 3 is a thin layer chromatogram demonstrating release of the drug, UC781, by reductive cleavage of the prodrug, PEG-S-S-UC781. Detection was by UV shadowing.
Figure 4:
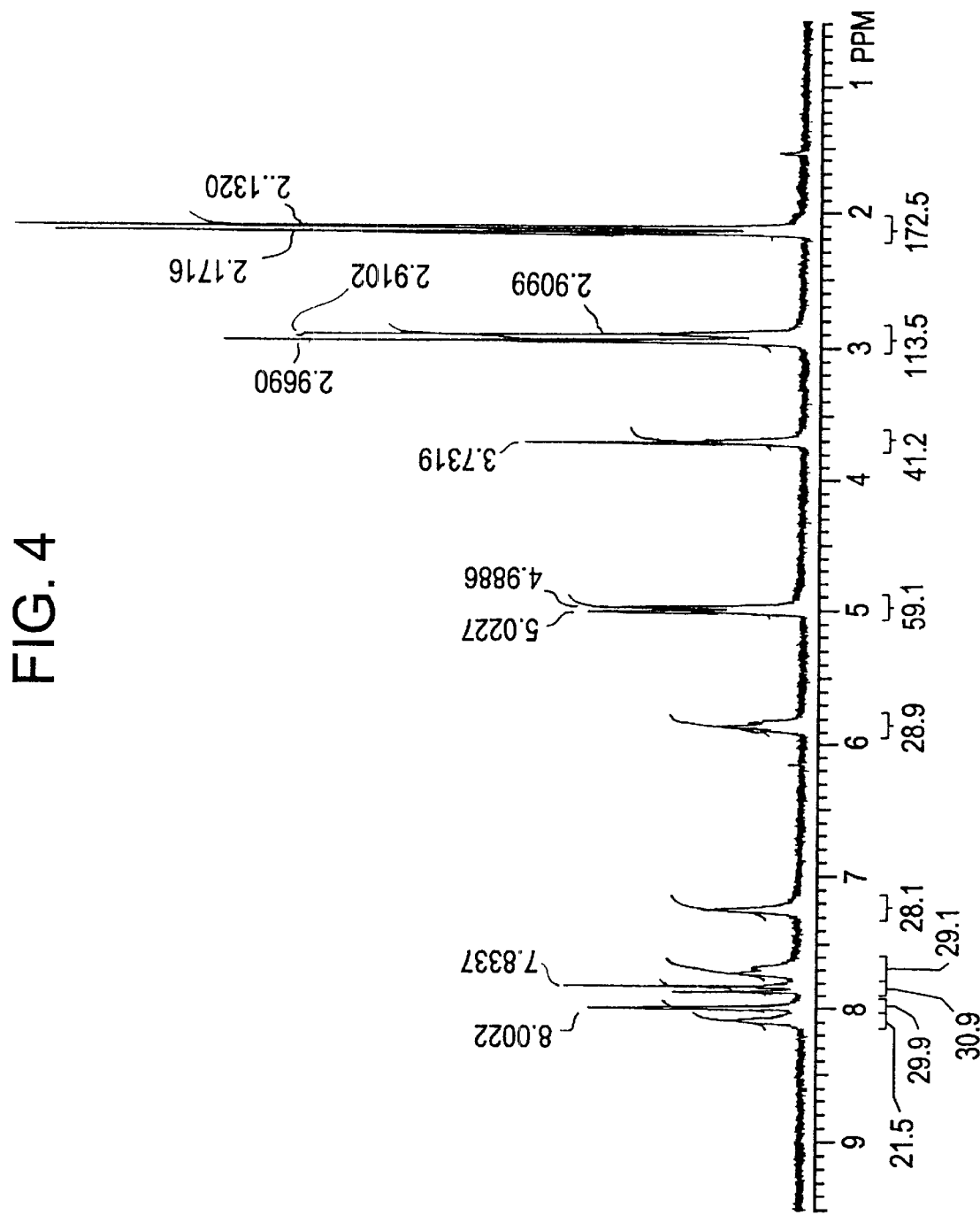
FIG. 4 depicts $^1$H NMR in deuterated dimethylsulfoxide of original UC781. The peak at about 3.7 ppm is due to water, and is not from the drug compound.
Figure 5:
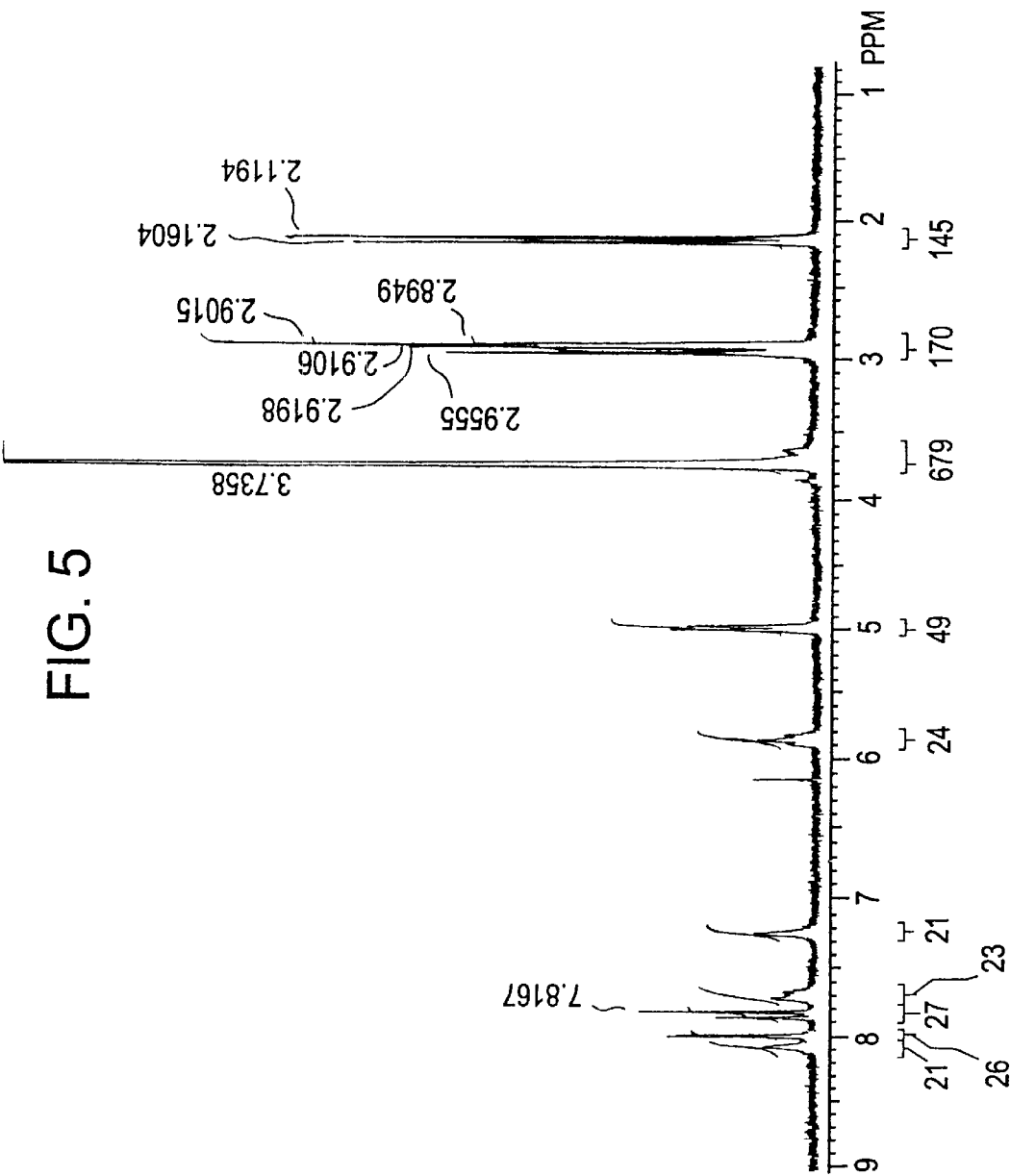
FIG. 5 shows $^1$H NMR in deuterated dimethylsulfoxide of UC781 regenerated from its prodrug conjugate, PEG-S-S-UC781. All peaks are the same as in FIG. 4. The peak at about 3.7 ppm is due to water, and is not from the drug compound.

III Release of UC781 from mPEG-S—S-UC781. In an organic phase reaction, the PEG-S—S-UC781 conjugate was dissolved in 0.5 ml of DCM. Then, 0.5 ml of 6 mM dithiothreitol (DTT) in DCM was added to the conjugate solution. After 2 hours, TLC showed a new spot at an Rf of 0.4, indicating that UC781 had been cleaved from the polymer (FIG. 3). The cleaved UC781 was purified by flash silica gel column and $^1$H NMR (FIGS. 4 and 5) showed the released product to be the same as the original UC781.

In an aqueous phase reaction, the PEG-S—S-UC781 conjugate was dissolved in 0.2 ml of phosphate-buffered saline (PBS), pH 7.4, and 0.2 ml of 6 mM glutathione was added to this solution. After 2 hours at room temperature, the reaction mixture was taken to dryness by speed vacuum. Then the dry residue was dissolved in DCM and TLC showed a spot with the same Rf of 0.4 as did the original UC781. The conclusion from these release studies is that the original drug, UC781, can be regenerated from its prodrug form, PEG-S—S-UC781, by reductive cleavage, including under conditions that might be found in a living cell.

EXAMPLE 2

Conjugate Synthesis by Means of an Intermediate Bifunctional Thiol Compound

In an alternate strategy to that described in Example 1 above, the UC781 homodimer is prepared as in Example 1, but then converted by disulfide exchange into a heterodimer with another bifunctional thiol compound, cysteamine, which also contains an amino group. This UC781 heterodimer is then appended to PEG by reaction of the amino group on the heterodimer with polyethylene glycol bis (imidazolyl carbonyl). By selecting the structure of the moiety next to the thiol group, the glutathione-induced release rate can be provided over a range of 2–3 orders of magnitude.

Synthesis of $NH_2$—$CH_2$—$C(CH_3)_2$—S—S—UC781: 133 mg of UC781 dimer (MW 670, 0.2 mmol) prepared as described in Example 1 was dissolved in 3 ml of degassed methylene chloride (degassed by bubbling with helium). Subsequently, 14 mg of 1-amino-2-methyl-2-propanethiol hydrochloride (MW 141.6, 0.1 mmol) was added to the solution. The reaction was kept under argon for 2 days. Thin Layer Chromatography (TLC) showed that all the 1-amino-2-methyl-2-propanethiol hydrochloride had reacted.

Coupling of $NH_2$—$CH_2$—$C(CH_3)_2$—S—S—UC781 to dicarboxy-PEG: The purified $NH_2$—$CH_2$—$C(CH_3)_2$—S—S—UC781 was reacted with polyethylene glycol bis (imidazolyl carbonyl) (Sigma Chemical Co.) having a polymer average molecular weight of 3,350 Daltons. The product was purified by ether precipitation.

In an alternate procedure to the above, cysteamine may be used in place of 1-amino-2-methyl-2-propanethiol, which produces a UC781 conjugate (PEG-CO—NH—$CH_2$—$CH_2$—S—S—UC781) with less sterically hindered thiol groups and therefore with a ~100-fold faster release under reducing conditions.

EXAMPLE 3

Synthesis of PEG-S—S-4-thiouridine

4-Thiouridine (MW 260, 8 mg, 0.031 mmol) was dissolved in 3 ml of acetonitrile and kept on ice. DIEA (5.3 µl, 0.031 mmol) was added to the solution. Then 2.9 mg of iodine was dissolved in 3 ml ice cold acetonitrile and added to the flask dropwise while stirring. The reaction was kept on ice. TLC (10% methanol/90% DCM) showed that the reaction was completed after 2 hours. The reaction mixture was dried by speed vacuum. Then 4 ml of water and 6 ml of acetonitrile, degassed by helium bubbling, were added to dissolve the salt. Then thiol-PEG (MW 5000, 30 mg, 0.006 mmol) was added to the reaction mixture and kept under argon at room temperature overnight. The reaction mixture was dried by speed vacuum. The product was extracted into DCM.

The formation of the 4-thiouridine homodimer by iodine oxidation and the disulfide exchange reaction to give the PEG-S—S-4-thiouridine conjugate proceeded similarly to the UC781 reactions. On TLC analysis, the thiouridine dimer migrated more slowly than the monomer (FIG. 6, lanes 1 and 2), but returned to the monomer position upon treatment with the reducing agent DTT (FIG. 6, lane 3). One notable difference from UC781 is that thiouridine is water-soluble, so water was used to dissolve the homodimer. As a result, the DIEA-iodide salt also dissolved, but its presence did not interfere with the subsequent disulfide exchange reaction to make the PEG-S—S—4-thiouridine conjugate (FIG. 6, lane 5).

As with PEG-S—S-UC781, the original 4-thiouridine could be reductively released from its disulfide conjugate by exposure to DTT (FIG. 6, lane 6). Lane 7 shows DTT alone.

EXAMPLE 4

HPLC Analysis and In-vivo Release

UC781 was analyzed using an HPLC reverse phase column, PRP-1 (Hamilton, Reno, Nev.), under the following condition: mobile phase A: 20% acetonitrile, mobile phase B: 90% acetonitrile, flow rate: 1 ml/min. Gradient: 0–2 min, 100% A; 2–20 min, linear gradient from 100% A to 100% B; 20–28 min, 100% B; 28—30 min, linear gradient from 100% B to 100% A; 30–35 min, 100% A. Under these experimental conditions, the retention time for UC781 is 24.2 min. The wavelength for detection of UC781 is 290 nm.

Since 1 mole of UC781 can be appended to 1 mole of PEG-SH, the maximum drug content of this conjugate is 335/5335=6.3% (w/w). Quantitation of drug content was done by measuring the amount of UC781 released from the PEG-S—S-UC781 conjugate. An aliquot (500 mg) of PEG-S—S-UC781 was treated with 30 mM DTT in acetonitrile for 2 hours. The treated sample was analyzed by RP-HPLC. The amount of UC781 released, based on the standard curve, was 13 µg. Since all of the disulfide-linked UC781 should be releasable by this procedure, the UC781 content in the conjugate is 2.6%. The discrepancy from the theoretical maximum of 6.3% most likely results from a large portion of the thiol-PEG molecules being otherwise oxidized, such as to PEG-S—S-PEG. Since this conjugate is readily soluble in water (PBS) at 100 mg/ml, the now-soluble drug concentration is about 3 mg/ml. Thus, imparting water solubility to an otherwise insoluble drug was achieved by making this prodrug form. This improvement in solubility by carrying out the method of the invention may be likewise achieved with other insoluble agents.

To each 1 ml sample of EDTA-treated rabbit blood, 2 ml of acetonitrile was added, mixed and kept on ice for 10 min. The mixture was centrifuged at 1000×g for 10 min. The supernatant was collected and an aliquot (300 µl) was injected into the reverse phase column. To evaluate the accuracy of UC781 analysis in blood samples, UC781 (10 µg) in 10 ml of dimethylsulfoxide (DMSO) was added to blood, mixed by vortexing and then kept at room temperature for 10 min. Similarly, 500 µg of PEG-S—S-UC781 in 50 µl of water was spiked into blood. After centrifugation, 400 µl of the supernatant was analyzed, either without or with DTT pretreatment (3 mM for 2 hours at room temperature).

Quantitation of UC781 and PEG-S—S-UC781 in extracted blood samples was by reverse phase HPLC with monitoring at 292 nm. UC781 elutes at 24.2 minutes. Sample analysis without prior reduction by DTT should give the concentration of free UC781 since the conjugated form does not give a peak at 24.2 minutes. Indeed, it has been observed that PEG conjugates in general tend to aggregate at the top of reverse phase HPLC columns. However, prior reduction with DTT should give the total concentration of UC781 since the conjugated UC781 is converted into the free form prior to HPLC. The dose-response curve for UC781 was linear from 0.1 μg to 10 μg. Recovery through the extraction procedure was determined by spiking a known amount of either free or conjugated UC781 into EDTA-treated rabbit blood prior to acetonitrile extraction. The recovery of UC781 was found to be 113%. The recovery of UC781 from spiked PEG-S—S-UC781 was found to be 107% with DTT treatment and 106% without DTT treatment, indicating that the disulfide bond in PEG-S—S-UC781 is readily cleaved during exposure to whole blood. That these recovery percentages are a little higher than 100% may be because UC781 is partially excluded from erythrocytes.

Figure 7:
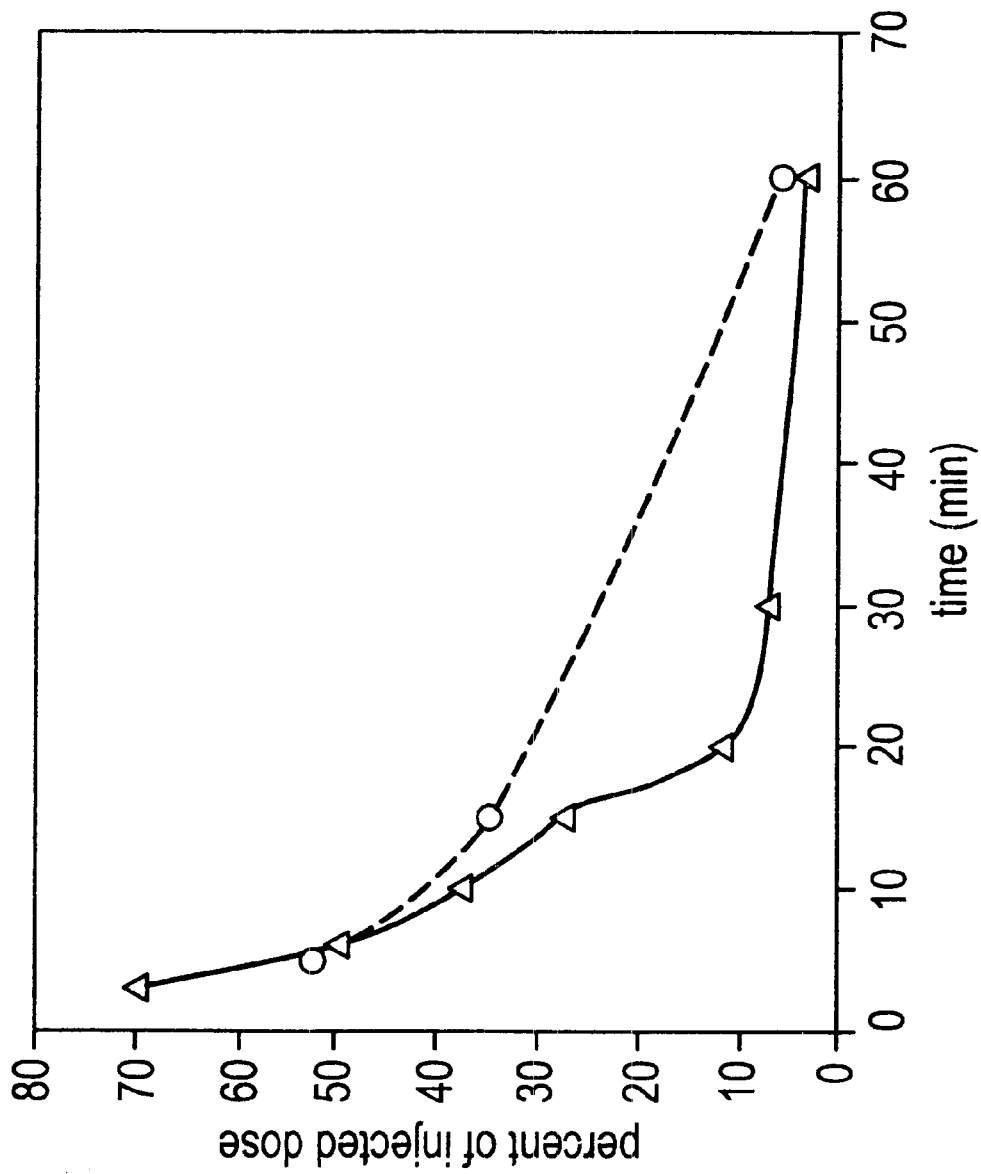
FIG. 7 depicts the kinetics following intravenous injection of PEG-S-S-UC781 in rabbits. Results from 2 separate rabbits are shown.

An in-vivo experiment was done in duplicate in rabbits (about 3.6 kg, New Zealand white, female), performed according to protocol #I99–054 approved by the IACUC of UMDNJ-Robert Wood Johnson Medical School. In detail, 55 mg of PEG-S—S-UC781 (equivalent to 1.5 mg of UC781) was dissolved in 1 ml of water, diluted into 5 ml of U.S.P. saline and injected intravenously into the marginal ear vein. Blood samples were drawn from the auricular artery of the opposite ear prior to and at predetermined time points after injection. Immediately after the blood was drawn, 1 ml was mixed with 2 ml of acetonitrile, vortexed, kept on ice for 10 min and then centrifuged at 1000×g for 10 min at 4° C. The supernatant was collected and analyzed by reverse phase HPLC, as described above. Blood levels were determined with time by HPLC with and without the DTT reductive cleavage step (FIG. 7). At every time point, the concentration of free UC781 was found to be the same in both the DTT-treated and the untreated samples, indicating, as anticipated, that UC781 had been rapidly released from its PEG carrier in vivo.

Estimating a total blood volume of 200 ml for the rabbits, then 52% and 70% of the total injected dose of PEG-S—S-UC781 is present in blood at the earliest time points, 5 min and 3 min, respectively in separate experiments. The half-life of UC781 in the bloodstream was found to be just several minutes (FIG.7). This data is consistent with the results given by Conover et al (6), in which the bioreversible ester-linked conjugate of PEG with the anticancer drug, camptothecin, had a blood $t_{1/2a}$ of less than 5 min. When plasma was prepared by centrifugation of a duplicate sample of EDTA-treated blood, the UC781 concentration was found to be about 10% higher than in the matched sample of whole blood, in agreement with the spiking experiment described above.

Figure 8:
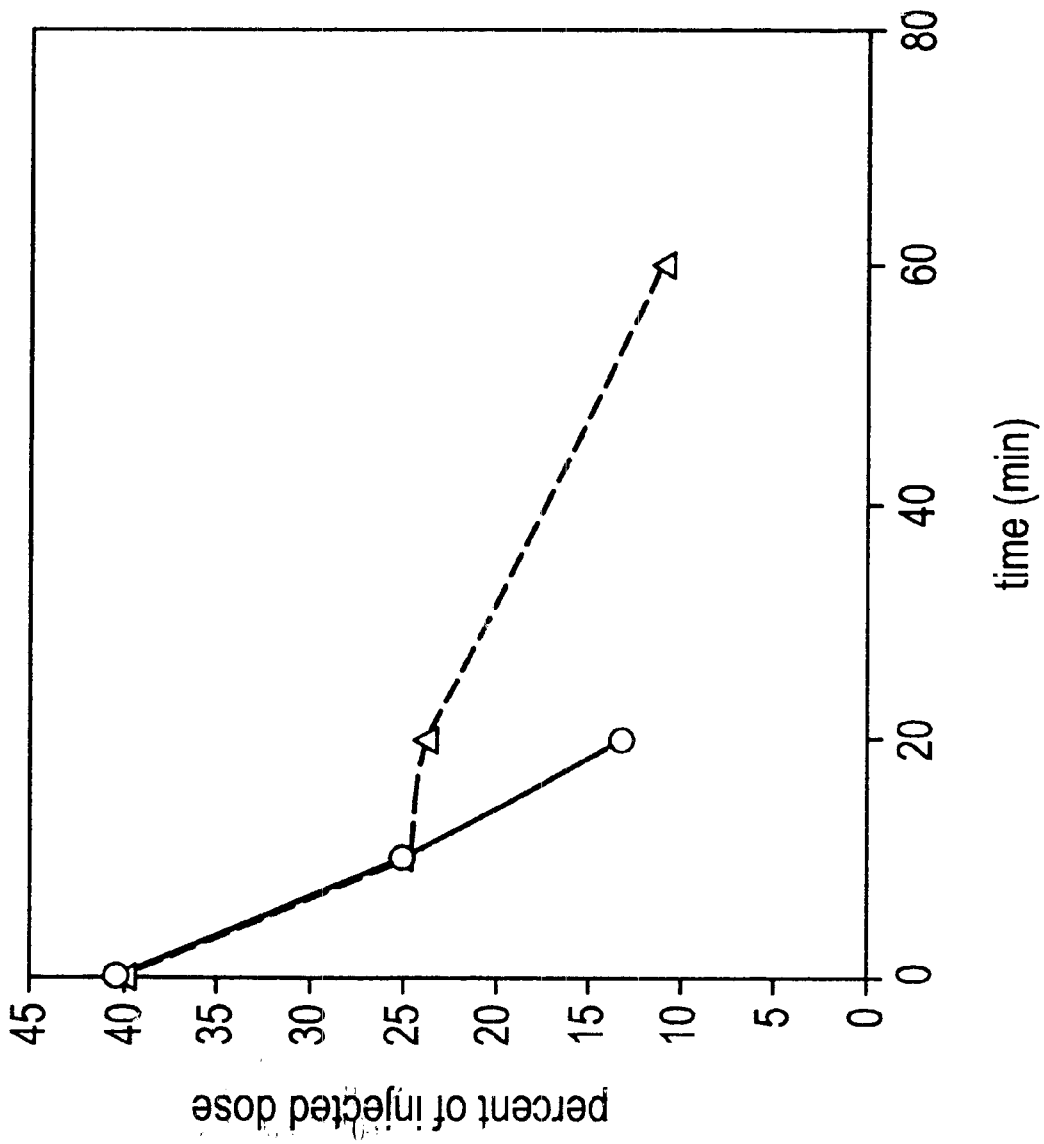
FIG. 8 depicts kinetics following intramuscular injection of PEG-S-S-UC781 in mice. Results from 2 separate mice are shown.

An in-vivo experiment was done twice in mice (about 25 g, Sprague-Dawley), performed according to protocol #I00–001, approved by the IACUC. PEG-S—S-UC781. Twenty mg, equivalent to 0.5 mg of UC781, was dissolved in 1 ml of PBS and injected into the leg muscle. At each time point, a mouse was euthanized, blood was collected and the injected muscle was removed. The blood samples were treated with 2 volumes of acetonitrile as described above. The tissue samples were homogenized with 1 ml of PBS and then treated with 2 volumes of acetonitrile, as above. The samples were then analyzed by reverse phase HPLC. As with the intravenous experiment, essentially the same values were obtained for UC781 whether or not the samples were pretreated with DTT. Recovery and extraction efficiency from the muscle was tested by injection into the excised muscle from a freshly euthanized mouse. This "zero" time point resulted in 40% recovery of the injected dose. As shown on FIG. 8, the half-time of diffusion of the drug from the muscle, assuming no metabolism in muscle, was about 10 minutes. Although there were relatively high levels of UC781 in the tissue samples even after 1 hour (more than 10%), blood samples were below the detection limit of the HPLC methods. This finding suggests that in mice the rate of elimination from the bloodstream is faster than the rate of diffusion from the injected muscle into the bloodstream.

EXAMPLE 5

Reverse Transcriptase (RT) Inhibition Assay

UC781 standard solutions were prepared in DMSO. The stock solution of HIV-RT (13.5 Units/μl) was diluted to 25 mUnits/μl in buffer comprising 50 mM Tris-HCl, pH 8.0, 1 mM DTT, 0.01% bovine serum albumin (BSA). Each assay tube contained 40 μl of a solution comprising 50 mM Tris-HCl, pH 8.0, 4 mM DTT, 12.4 mM MgCl2, 50 mM KCl, 0.01% BSA, 10 μg/ml poly(A), 0.01 mM dTTP and 10 mCi [$\alpha$-$^{32}$P]dTTP, 2 μl of diluted RT and 3 μl of sample dissolved in DMSO. Samples were incubated at 37° C. for 30 minutes. The polymerization reaction was stopped by adding 0.15 mg/ml of salmon sperm DNA and chilling on ice. An aliquot (20 μl) of each reaction mixture was spotted onto square stamped GF/C filter paper (12.5 cm in diameter) presoaked with 10% trichloroacetic acid (TCA). After the spots were dry, the paper was rinsed with 50 ml of ice cold 10% TCA twice, 50 ml of ice cold water three times and then once with 25 ml of ice cold 95% ethanol in a Buchner funnel. The paper was dried, cut into squares and each square was counted in 4 ml of LSC cocktail (National Diagnostics).

Figure 9:
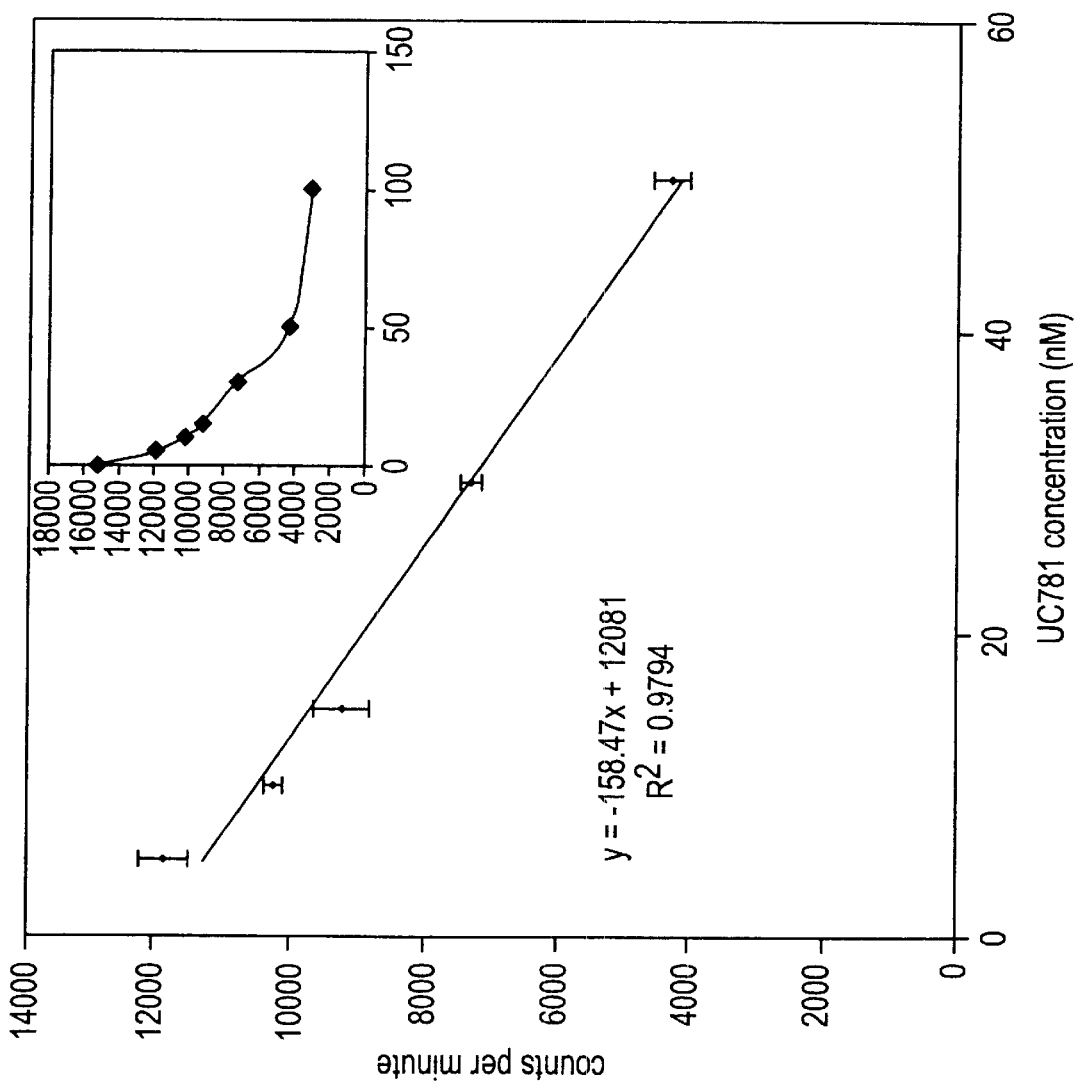
FIG. 9 shows dose-response graphs for reverse transcriptase inhibition assay. The main panel is a replot of the linear range data taken from the inset panel.

The reverse transcriptase inhibition (RT) assay was used to confirm that the compound released in blood is truly active UC781. The peak fraction at 24.2 minutes was collected from the HPLC analysis of a sample of blood collected at the 5 minute time point from the intravenous injection of PEG-S—S-UC781. As a control, authentic UC781 was run on the HPLC column and the peak was collected at 24.2 minutes. As shown in FIG. 9, the RT assay is linear with inhibitor concentration in the range of 5 nM to 50 nM UC781. An aliquot of each HPLC fraction, providing a predicted concentration of 30 nM in the RT assay, was analyzed. The RT assay gave results of 26 nM and 27 nM for the blood and standard samples, respectively, indicating that the recovered compound is fully active.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

1. Herold, D. A., Keil, K. and Bruns, D. E. (1989) Oxidation of polyethylene glycols by alcohol dehydrogenase. Biochem. Pharmacol. 38, 73.

2. Smyth, Jr., H. E., Carpenter, C. P. and Weil, C. S. (1950) The toxicology of the polyethylene glycols. J. Am. Pharm. Assoc. 39, 349.

3. Johnson, A. J., Dapatkin, M. H. and Newman, J (1971) Clinical investigation of intermediate and high-purity anti-haemophilic factor concentration. Br. J. Hematol. 21, 21.

4. Davis, S., Abuchowski, A., Park, Y. K., and Davis F. F. (1981) Alteration of the circulating half-life and antigenic properties of bovine adenosine deaminase in mice by attachment of poly(ethylene glycol). Clin. Exp. Immunol. 46, 649–652.

5. Greenwald, R. B., Gilbert, C. W., Pendri, A., Conover, C. D., Xia, J. and Martinez, A. (1996) Drug delivery systems: Water soluble taxol 2'-poly(ethylene glycol) ester prodrugs-Design and in vivo effectiveness. J. Med. Chem. 39, 424–431.

6. Conover, C. D., Pendri, A., Gilbert, C. W., Shum, K. L. and Greenwald, R. B. (1997) Camptothecin delivery system: The antitumer activity of a camptothecin-20-0-polyethylene glycol ester transport form. Anticancer Res. 17, 3361–3368.

7. Francis G. E., Delgado C., Fisher D., Malik F., Agrawal A. K. (1996) Polyethylene glycol modification: relevance of improved methodology to tumor targeting. J. Drug Targeting, 3, 321–40.

8. Zalipsky, S. (1995) Functionalized poly(ethylene glycol) for preparation of biologically relevant conjungates. Bioconj.Chem. 6, 150–165.

9. Nathan, A., Zalipsky, S., Ertel, S. I., Agathos, S. N., Yarmush, M. L. and Kohn, J. (1993) Copolymers of lysine and poly(ethylene glycol): A new family of functionalized drug carriers. Bioconj. Chem. 4, 54–62.

10. Huang, S., Pooyan S., Wang, J., Choudhury, I., Leibowitz, M. J., and Stein, S. (1998) A polyethylene glycol copolymer for carrying and releasing multiple copies of cysteine-containing peptides, Bioconj. Chem. 9, 612–617.

11. De Clercq, E. (1993) HIV-1 specific RT inhibitors: highly selective inhibitors of human immunodeficiency virus type 1 that are specifically targeted at the virus reverse transcriptase. Med. Res. Rev. 13, 229–258.

12. Borkow, G., Arion, D., Wainberg, M. A. and Parniack, M. A. (1999) The Thiocarboxanilide Nucleoside Inhibitor UC781 Restores antiviral activity of 3'-Azido-3'-Deoxythymidine (AZT) against AZT-resistant HIV-1. Antimicrobial Agents and Chemotherapy 43, 259–263.

13. Zabicky, J. The Chemistry of Amides, P449, Interscience Publishers (1970).

14. Schaeffer, J. R., Goodhue, C. T., Risley, H. A. and Stevens, R. E. (1967) The synthesis, stability and sulfur-elimination reactions of some Bis(N-arylimidoyl) disulfides, J. of Org. Chem. 32, 392.

15. Pauwels, R., Andries, K., Desmyter, J., Schols, D., Kukla, M. J., Breslin, H. J., Raemaeckers, A., Van Gelder, J., Woestenborghs, R., Heykants, J., Schellekens, K., Janssen, M. A. C., De Clercq, E. and Janssen, P. A. J. (1990) Potent and selective inhibition of HIV-1 replication in vitro by a novel series of TIBO derivatives. Nature 343, 470–474.

16. Kleim, J. -P. et al. (1997) In vitro selection for different mutational patterns in the HIV-1 reverse transcriptase using high and low selective pressure of the nonnucleoside reverse transcriptase inhibitor HBY 097. Virology 231, 112–118.

17. Matthes, E., Lehmann, C., Von Janda-Lipinski, M. and Scholz, D. (1989) Inhibition of HIV replication by 3'-fluoro-modified nucleosides with low cytotoxicity. Biochem. Biophys. Res. Commun. 165, 488–495.

18. Borkow, G., Barnard, J., Nguyen, T. M., Belmonte, A., Wainberg, M. A., Parniak, M. A. Chemical barriers to human immunodeficiency virus type 1 (HIV-1) infection: Retrovirucidal activity of UC781, a thiocarboxanilide nonnucleoside inhibitor of HIV-1 reverse transcriptase. J. Virol. 71, 3023–3030.

19. Woghiren, C., Sharma, B. and Stein, S. (1993) Protected thiol-polyethylene glycol: A new activated polymer for reversible protein modification. Bioconj. Chem. 4, 314–318.

What is claimed is:

1. A pharmaceutical composition comprising a disulfide-linked conjugate of at least one therapeutic agent comprising prior to conjugation a thioamide moiety, and at least one polymer comprising prior to conjugation at least one thiol group.

2. The composition of claim 1 wherein said polymer comprising prior to conjugation at least one thiol group is a conjugate of a polymer comprising at least one functional group and a bifunctional compound comprising at least one functional group and at least one thiol group, said at least one functional group of said polymer linked to at least one said functional group of said bifunctional compound.

3. The composition of claim 1 wherein said polymer comprising prior to conjugation at least one thiol group has a polymer backbone selected from the group consisting of polyethylene glycol, carboxymethylcellulose, dextran, polyvinyl alcohol, N-(2-hydroxypropyl)methacrylamide, polyvinyl pyrrolidone, poly-1,3-dioxolane, poly-1,3,6-trioxane, polypropylene oxide, copolymers of ethylene/maleic anhydride copolymer, polylactide/polyglycolide copolymers, polyaminoacids, copolymer of polyethylene glycol and an amino acid, and polypropylene oxide/ethylene oxide copolymers.

4. The composition of claim 1 wherein said polymer comprising prior to conjugation at least one thiol group is a branched polymer or a dendrimer.

5. The composition of claim 3 wherein said polymer backbone is a polyethylene glycol polymer.

6. The composition of claim 5 wherein said polyethylene glycol polymer has a molecular weight of from about 300 to about 30,000 Da.

7. The composition of claim 6 wherein said polyethylene glycol polymer has a molecular weight of from about 600 to about 5,000 Da.

8. The composition of claim 1 wherein said polymer comprising prior to conjugation at least one thiol group has a polymer backbone selected from the group consisting of a polyethylene glycol-thiomalic acid copolymer, a polyethylene glycol-cysteamine conjugate, a polyethylene glycol-1-amino-2-methyl-2-propanethiol conjugate, and a polyethylene glycol-lysine conjugate wherein free carboxy groups on said lysine are derivatized to form thiol groups.

9. The composition of claim 2 wherein said polymer comprising at least one functional group is selected from the group consisting of α,ω-dihydroxy-polyethylene glycol; α,ω-dicarboxy-polyethylene glycol; and α,ω-diamino-polyethylene glycol.

10. The composition of claim 1 wherein said polymer comprising prior to conjugation at least one thiol group has from one to about ten thiol groups per polymer.

11. The composition of claim 10 wherein said polymer comprising prior to conjugation at least one thiol group has from one to about three thiol groups per polymer.

12. The composition of claim 1 wherein said therapeutic agent is selected from the group consisting of UC781; R82150; HBY097; S2720; thiouridine; UC38, trovirdine and 2',3'-dideoxy-3'-fluoro-4-thiothymidine.

13. The composition of claim 1 wherein said therapeutic agent is derivatized to comprise a thioamide moiety.

14. The composition of claim 1 wherein said polymer additionally comprises a functional group.

15. The composition of claim 14 wherein said additional functional group is derivatized with a compound selected from the group consisting of an antibody, a cell uptake enhancer, and a tissue targeting agent.

16. The composition of claim 1 wherein the thiol group on said polymer comprising at least one thiol group is sterically hindered.

17. The composition of claim 16 wherein said sterically hindered thiol group decreases the susceptibility of said conjugate to cleavage under reducing conditions.

18. The composition of claim 1 comprising a second therapeutic agent.

19. The composition of claim 18 comprising a third therapeutic agent.

20. The composition of claim 1 wherein said therapeutic agent is released in vivo under reducing conditions.

21. The composition of claim 1 wherein the in-vivo half life of said therapeutic agent in said composition is increased compared with that of the therapeutic agent alone in vivo.

22. The composition of claim 1 wherein said therapeutic agent is therapeutically inactive or weakly active in said composition.

23. The composition of claim 1 wherein the water solubility of said therapeutic agent is increased in said composition compared to its inherent water solubility.

24. A method for preparing a composition comprising a disulfide-linked conjugate of at least one therapeutic agent comprising prior to conjugation a thioamide moiety, and at least one polymer comprising prior to conjugation at least one thiol group, comprising the steps of:
   a) providing said at least one therapeutic agent comprising a thioamide moiety;
   b) providing said at least one polymer comprising a thiol group;
   c) reacting said at least one therapeutic agent comprising a thioamide moiety under oxidizing conditions to form at least one disulfide cross-linked homodimer of said at least one therapeutic agent comprising a thioamide moiety;
   d) reacting said at least one disulfide-linked homodimer with said at least one polymer comprising a thiol group, under conditions in which a disulfide exchange reaction occurs, to form a disulfide-linked disulfide-linked conjugate of at least one therapeutic agent comprising prior to conjugation a thioamide moiety, and at least one polymer comprising prior to conjugation at least one thiol group; and
   e) isolating said at least one disulfide-linked conjugate of at least one therapeutic agent comprising prior to conjugation a thioamide moiety, and at least one polymer comprising prior to conjugation at least one thiol group.

25. The method of claim 24 wherein said polymer comprising at least one thiol group is a conjugate of a polymer comprising at least one functional group and a bifunctional compound comprising at least one functional group and at least one thiol group, said at least one functional group of said polymer linked to at least one said functional group of said bifunctional compound.

26. The method of claim 24 wherein said polymer comprising a thiol group is a branched polymer or a dendrimer.

27. The method of claim 24 wherein said polymer comprising a thiol group has a polymer backbone selected from the group consisting of polyethylene glycol, carboxymethylcellulose, dextran, polyvinyl alcohol, N-(2-hydroxypropyl)methacrylamide, polyvinyl pyrrolidone, poly-1,3-dioxolane, poly-1,3,6-trioxane, polypropylene oxide, copolymers of ethylene/maleic anhydride copolymer, polylactide/polyglycolide copolymers, polyaminoacids, copolymer of polyethylene glycol and an amino acid, and polypropylene oxide/ethylene oxide copolymers.

28. The method of claim 27 wherein said polymer backbone is a polyethylene glycol polymer.

29. The method of claim 28 wherein said polyethylene glycol polymer has a molecular weight of from about 300 to about 30,000 Da.

30. The method of claim 29 wherein said polyethylene glycol polymer has a molecular weight of from about 600 to about 5,000 Da.

31. The method of claim 24 wherein said polymer comprising at least one thiol group is selected from the group consisting of a polyethylene glycol/thiomalic acid conjugate, a polyethylene glycol/cysteamine conjugate, and a polyethylene glycol/1-amino-2-methyl-2-propanethiol conjugate.

32. The method of claim 25 wherein said polymer comprising at least one functional group is selected from the group consisting of $\alpha,\omega$-diamino-polyethylene glycol; $\alpha,\omega$-dihydroxy-polyethylene glycol; and $\alpha,\omega$-dicarboxy-polyethylene glycol.

33. The method of claim 24 wherein said polymer comprising at least one thiol group has from one to about ten thiol groups per polymer.

34. The method of claim 33 wherein said polymer comprising at least one thiol group has from one to about three thiol groups per polymer.

35. The method of claim 24 wherein said therapeutic agent is selected from the group consisting of UC781; R82150; HBY097; S2720; thiouridine; UC-38, trovirdine and 2',3'-dideoxy-3'-fluoro-4-thiothymidine.

36. The method of claim 24 wherein said therapeutic agent is derivatized to comprise a thioamide moiety.

37. The method of claim 24 wherein said oxidizing conditions comprises reaction in the presence of an oxidizing agent selected from the group consisting of molecular oxygen, hydrogen peroxide, and molecular iodine.

38. The method of claim 24 wherein the reaction conditions of step (d) comprise a degassed nonaqueous solvent.

39. The method of claim 38 wherein said solvent is a 1:1 mixture of dimethylformnamide and dichloromethane.

40. The method of claim 24 wherein said polymer additionally comprises a functional group.

41. The method of claim 40 wherein said additional functional group is derivatized with a compound selected from the group consisting of an antibody, a cell uptake enhancer or a tissue targeting agent.

42. The method of claim 24 wherein the thiol group on said polymer comprising a thiol group is sterically hindered.

43. The method of claim 24 wherein said composition comprises a second therapeutic agent.

44. The method of claim 43 wherein said composition comprises a third therapeutic agent.

45. The method of claim 24 wherein said therapeutic agent is released in vivo under reducing conditions.

46. The method of claim 24 wherein the in-vivo half life of said therapeutic agent in said composition is increased compared with that of the therapeutic agent alone in vivo.

47. The method of claim 24 wherein said therapeutic agent is therapeutically inactive or weakly active in said composition.

48. The method of claim 24 wherein the water solubility of said therapeutic agent is increased in said composition compared to its inherent water solubility.

49. The method of claim 24 wherein said disulfide-linked agent polymer conjugate is entrapped in a matrix providing a controlled release depot.

50. A method for preparing a composition comprising a disulfide-linked conjugate of at least one therapeutic agent comprising prior to conjugation a thioamide moiety, and at least one polymer comprising prior to conjugation at least one thiol group, comprising the steps of:

a) providing said at least one therapeutic agent comprising a thioamide moiety;
b) providing a bifunctional thiol-containing compound, said compound comprising at least one functional group other than said thiol group;
c) providing a polymer with a functional group;
d) reacting said at least one therapeutic agent comprising a thioamide moiety under oxidizing conditions to form at least one disulfide cross-linked homodimer of said at least one therapeutic agent comprising prior to said reacting a thioamide moiety;
e) reacting said at least one disulfide-linked homodimer with said bifunctional thiol-containing compound under conditions in which a disulfide exchange reaction occurs to form a disulfide-linked heterodimer of said at least one therapeutic agent comprising prior to said reacting a thioamide moiety and said bifunctional thiol-containing compound;
f) reacting said disulfide-linked heterodimer with said polymer with a functional group to form a covalent conjugate thereof comprising a therapeutic agent comprising prior to said reacting a thioamide moiety and said polymer comprising a thiol group; and
g) isolating said at least one disulfide-linked conjugate of said at least one therapeutic agent comprising a thioamide moiety, and said at least one polymer comprising a thiol group.

51. A method for the controlled release in an animal of at least one therapeutic agent comprising prior to conjugation a thioamide moiety comprising administering to said animal a composition comprising at least one pharmaceutical composition of claim 1.

52. The method of claim 51 wherein said composition comprises a second therapeutic agent.

53. The method of claim 52 wherein said composition comprises a third therapeutic agent.

54. The method of claim 50 wherein said therapeutic agent is released in vivo under reducing conditions.

55. The method of claim 50 wherein the in-vivo half life of said therapeutic agent in said animal is increased compared with that of the therapeutic agent alone in said animal.

56. The method of claim 50 wherein said therapeutic agent is therapeutically inactive or weakly active in said composition.

57. A method for the controlled release in an animal of a therapeutic agent within a preselected body compartment comprising administering to said animal the composition of claim 1, said composition additionally comprising a targeting agent for targeting said composition to said compartment.

58. The method of claim 57 wherein said targeting agent is selected from the group consisting of an antibody, a cell uptake enhancer, and a tissue targeting agent.

59. A method for the controlled release in an animal of at least one therapeutic agent comprising prior to conjugation a thioamide moiety comprising administering to said animal a composition comprising at least one pharmaceutical composition of claim 2.

* * * * *